United States Patent [19]

Feder et al.

[11] Patent Number: 4,927,630
[45] Date of Patent: * May 22, 1990

[54] TISSUE PLASMINOGEN ACTIVATOR FROM NORMAL HUMAN COLON CELLS

[75] Inventors: Joseph Feder, University City; Susan C. Howard, Fenton; Arthur J. Wittwer, Ellisville, all of Mo.; Thomas W. Rademacher, Oxford, United Kingdom; Raj B. Parekh, Oxford, United Kingdom; Raymond A. Dwek, Oxford, United Kingdom

[73] Assignee: Monsanto Company, St. Louis, Mo.

[*] Notice: The portion of the term of this patent subsequent to Jun. 14, 2005 has been disclaimed.

[21] Appl. No.: 167,946

[22] Filed: Mar. 11, 1988

Related U.S. Application Data

[63] Continuation-in-part of Ser. No. 929,950, Nov. 11, 1986, Pat. No. 4,751,084, which is a continuation-in-part of Ser. No. 834,080, Feb. 26, 1986, abandoned.

[51] Int. Cl.$^5$ .................. C12N 9/48; C12N 9/50; A61K 37/547
[52] U.S. Cl. .................. 424/94.64; 424/94.63; 514/8; 514/54; 514/822; 435/212; 435/219; 530/395; 536/123
[58] Field of Search .......... 514/8; 424/94.64; 435/212, 68, 219; 530/395

[56] References Cited

U.S. PATENT DOCUMENTS

| | | | |
|---|---|---|---|
| 3,904,470 | 9/1975 | Hull et al. | 435/215 |
| 4,190,708 | 2/1980 | Kuo et al. | 435/215 |
| 4,335,215 | 6/1982 | Tolbert et al. | 435/241 |
| 4,505,893 | 3/1985 | Mori et al. | 424/94 |
| 4,537,860 | 8/1985 | Tolbert et al. | 435/240 |
| 4,550,080 | 10/1985 | Hasegawa et al. | 435/212 |
| 4,751,084 | 6/1988 | Feder et al. | 514/8 |

FOREIGN PATENT DOCUMENTS

| | | |
|---|---|---|
| 41766 | 12/1981 | European Pat. Off. . |
| 117059 | 8/1984 | European Pat. Off. . |
| 238304 | 3/1987 | European Pat. Off. . |
| 2119804 | 11/1983 | United Kingdom . |

OTHER PUBLICATIONS

Rijkin and Collen, J. Biol. Chem. 256 (13), 7035–41 (1981).
Kluft et al., Adv. Biotech. Proc. 2, Alan R. Liss, Inc., 1983, pp. 97–110.
Ranby et al., FEBS Lett. 146(2), 289–92 (1982).
Wallen et al., Eur. J. Biochem. 132, 681–6 (1983).
Pohl et al., Biochemistry 23, 3701–07 (1984).
Pohl et al., EMBO Workshop on Plasminogen Activators, Amalfi, Italy, Oct. 14–18, 1985.
Pernica et al., Nature 301, 214–21 (1983).
Vehar et al., Biotech 2(12), 1051–57 (1984).
Collen et al., Circulation 70(16), 1012–17 (1984).
Little et al., Biochemistry 23, 6191–95 (1984).
Opdenakkher et al., EMBO Workshop supra.
Brouty-Boye et al., Biotech. 2(12) 1058–62 (1984).
Pohl et al., FEBS Lett. 168(1), 29–32 (1984).
Kaufman et al., Mol. Cell. Biol. 5, 1750–59 (1985).
Browne et al., Gene 33, 279–84 (1985).
Zamarron et al., J. Biol. Chem. 259(4), 2080–83 (1984).
Collen et al., J. Pharmacol. Expertl. Therap. 231(1), 146–52 (1984).
Rijken et al., Biochem. Biophys. Acta 580, 140–153 (1979).
Husain et al., Proc. Natl. Acad. Sci. U.S.A. 78(7), 4265–69 (1981).
Schleef et al., Thromb. Haemos. 53(1), 170–175 (1985).
Corasanti et al., J. Natl. Cancer Inst. 65(2), 345–351 (1980).
Tissot and Bachman, Prog. Fibrinolysis 6, 133–135 (1983).
Tissot et al., Int. J. Cancer 34, 295–302 (1984).
Pohl et al., Eur. J. Biochem. 170(½), 69–75 (1987).
Einarsson et al., Biochim. Biophys. Acta 830, 1–10 (1985).
Rijken et al., Thromb. & Haemostas. 54(4), 788–791 (1985).

Primary Examiner—Jacqueline Stone
Attorney, Agent, or Firm—Scott J. Meyer; James W. Williams, Jr.

[57] ABSTRACT

Normal human colon fibroblast tissue plasminogen activator is separated by lysine-Sepharose affinity chromatography into Types I and II glycoforms and characterized with respect to the relative incidence of each type of oligosaccharide comprising the respective Types I and II glycoforms.

3 Claims, 11 Drawing Sheets

TISSUE PLASMINOGEN ACTIVATOR FROM NORMAL HUMAN COLON CELLS

CROSS-REFERENCE TO RELATED APPLICATION

This is a continuation-in-part of copending application Ser. No. 929,950, filed Nov. 11, 1986 now U.S. Pat. No. 4,751,084, which, in turn, is a continuation-in-part of application Ser. No. 834,080, filed Feb. 26, 1986 and now abandoned.

BACKGROUND OF THE INVENTION

This invention relates to plasminogen activators which are useful thrombolytic agents. More particularly, this invention relates to glycosylated tissue plasminogen activator from cultured normal human colon cells.

In copending application Ser. No. 929,950, filed Nov. 11, 1986, now U.S. Pat. No. 4,751,084, a novel tissue plasminogen activator (t-PA) is disclosed which has a unique glycosylation pattern and which is derived from normal human colon fibroblast cells.

A group of sixteen different oligosaccharides were identified and characterized as forming part of the sugar moiety of the glycoprotein.

The normal human colon fibroblast t-PA was further characterized in terms of the Type I and Type II glycoforms. In Type I the t-PA protein moiety of 527 amino acids is glycosylated at Asn-117, Asn-184 and Asn-448; whereas, in Type II the glycosylation occurs at Asn-117 and Asn-184. The relative incidence of complex, hybrid and oligomannose structures in each of the Type I and Type II t-PA glycoproteins is shown.

BRIEF DESCRIPTION OF THE INVENTION

In accordance with the present invention, normal human colon fibroblast tissue plasminogen activator (t-PA) is separated by affinity chromatography on lysine-Sepharose into Type I and Type II glycoproteins and is characterized with respect to the relative incidence of each type of oligosaccharide comprising the respective Type I and Type II glycoforms.

As used herein, the normal human colon fibroblast t-PA is that defined in copending application Ser. No. 929,950, filed Nov. 11, 1986, now U.S. Pat. No. 4,751,084. In a preferred embodiment of the invention the t-PA is isolated from the normal human colon fibroblast cell line CCD-18Co. This cell line is on deposit without restriction in the permanent collection of the American Type Culture Collection, Rockville, Md, under accession number ATCC CRL-1459. Samples of the cell line can be obtained by the public upon request to that depository.

The unfractionated t-PA can be prepared and purified as described in said copending application Ser. No. 929,950, now U.S. Pat. No. 4,751,084, and in copending application Ser. No. 849,933, filed Apr. 9, 1986 now abandoned. The corresponding European Patent Applications were published on Sept. 9, 1987 as EP 236,289 and on Oct. 14, 1987 as EP 241,448, respectively. Said applications are assigned to a common assignee and their disclosures are incorporated herein by reference.

According to the present invention, the unfractionated t-PA is separated into Type I and Type II glycoproteins by affinity chromatography on lysine-Sepharose. The use of said affinity chromatography for separation of Types I and II t-PAs derived from Bowes melanoma is described by Einarsson et al., *Biochim. Biophys. Acta* 830, 1–10 (1985), and Rijken et al., *Thromb. and Haemostas.* 54(4), 788–791 (1985). A preferred such material for use herein is Lysine-Sepharose ® 4B which is commercially available from Pharmacia (Piscataway, N.J.).

As used herein, the colon t-PA oligosaccharide structures and nomenclature are as defined in said copending application Ser. No. 929,950. The relevant incidence of each of these oligosaccharides comprising the respective Type I and Type II glycoforms in the t-PA fractionated on the lysine-Sepharose and compared to that of the unfractionated t-PA is about as shown in Table I, below. The values are rounded to the nearest whole number and are estimated to be subject to variation of ± one unit of the values shown.

TABLE I

| Oligosaccharide | % Type I | % Type II | % Unfractionated |
|---|---|---|---|
| C-A | 2 | 2 | 1 |
| C-B | 9 | 10 | 7 |
| C-C-1 | 12 | 10 | 11 |
| C-C-2 | 3 | 3 | 3 |
| C-C-3 | 2 | 1 | 2 |
| C-C-4 | 2 | 1 | 1 |
| C-D-1 | 5 | 3 | 5 |
| C-D-2 | 17 | 9 | 15 |
| C-E | 13 | 9 | 12 |
| C-F | 6 | 5 | 6 |
| C-G-1 | 3 | 6 | 4 |
| C-G-2 | 3 | 3 | 2 |
| C-G-3 | 4 | 5 | 4 |
| C-H | 9 | 18 | 14 |
| C-I | 8 | 14 | 12 |
| C-J | 3 | 3 | 3 |

After the fractionation into Type I and Type II t-PAs, the separated fractions can be recombined in any proportion to provide any desired % of Type I and Type II glycoforms. Thus, based on the above values which are subject to the variation of ± one unit, the % of oligosaccharide C-A can range from about 1 to about 3, the % of oligosaccharide C-B can range from about 8 to about 11, the % of oligosaccharide C-C-1 can range from about 9 to 13, and so forth with the other thirteen oligosaccharides. As indicated in FIG. 1, described hereinafter, the fractions comprising the Type I and Type II t-PAs do not represent the entire unfractionated t-PA. Therefore, the % of the oligosaccharides in the unfractionated t-PA need not be equal to the sum of the individual Type I and Type II t-PA components shown in Table I.

The structures of the sixteen oligosaccharides are as follows:

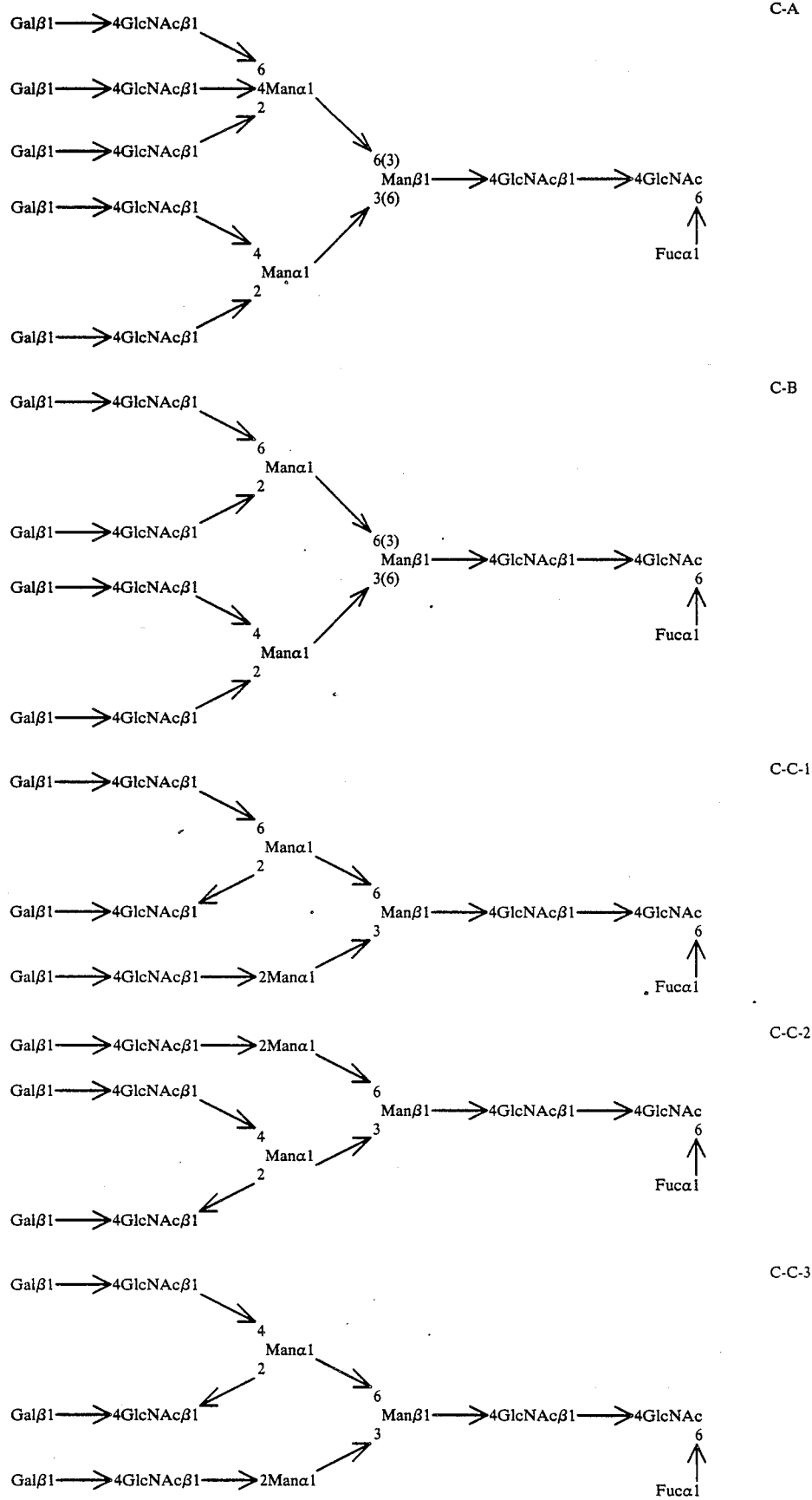

C-C-4
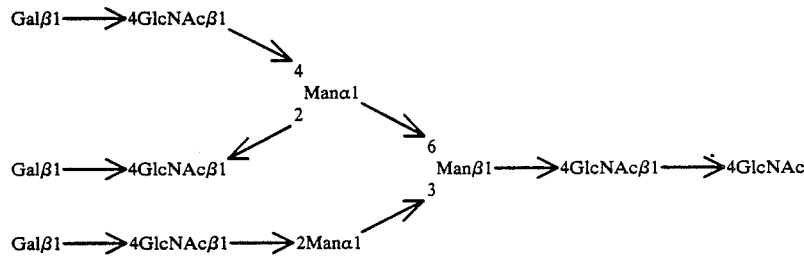
C-D-1
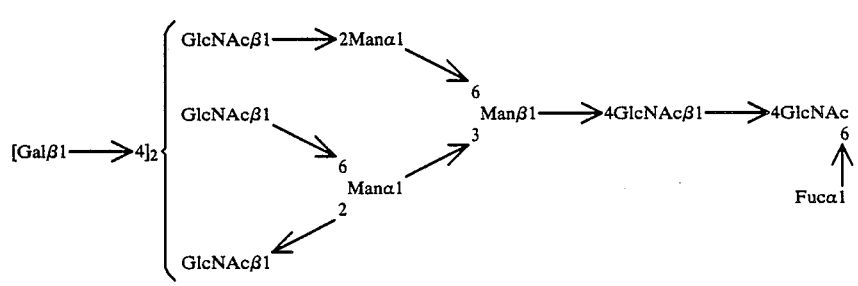
C-D-2
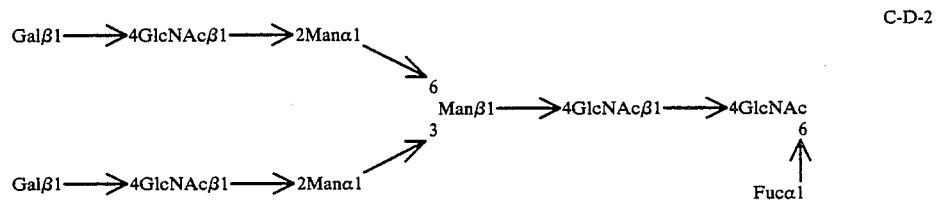
C-E
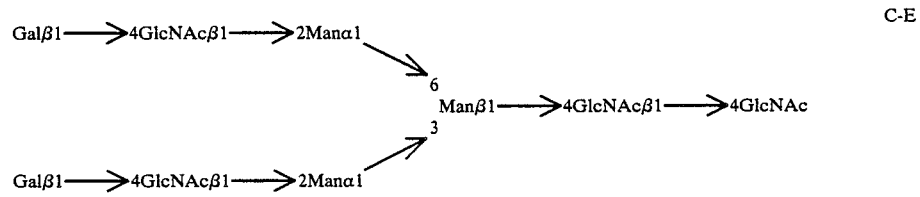
C-F
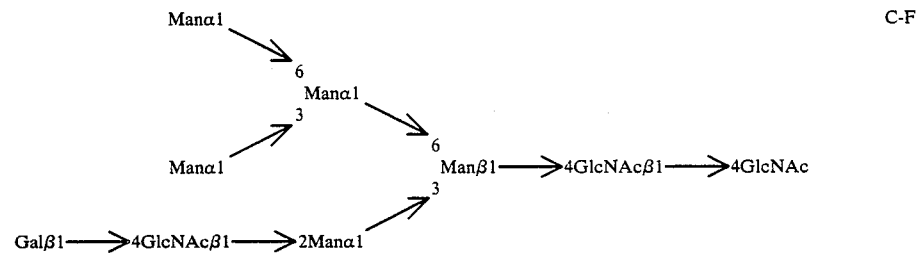
C-G-1
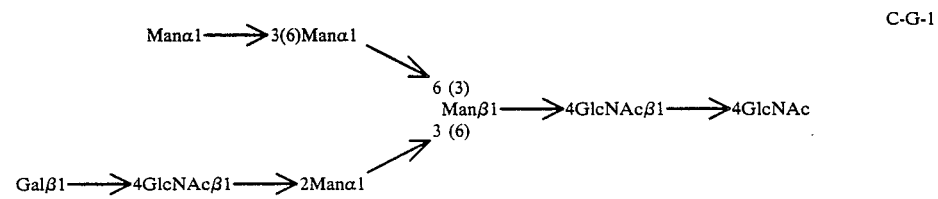
C-G-2
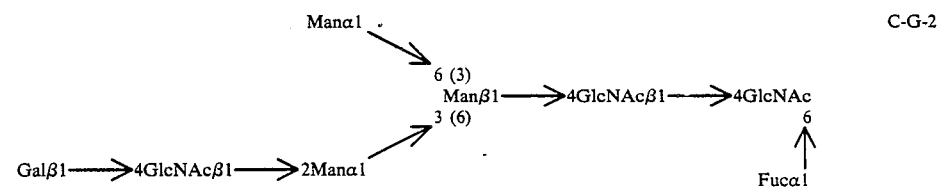

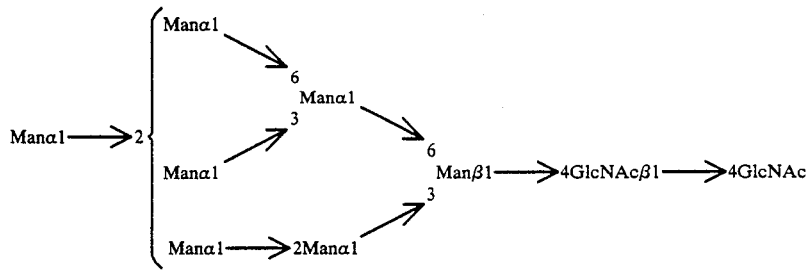

C-G-3

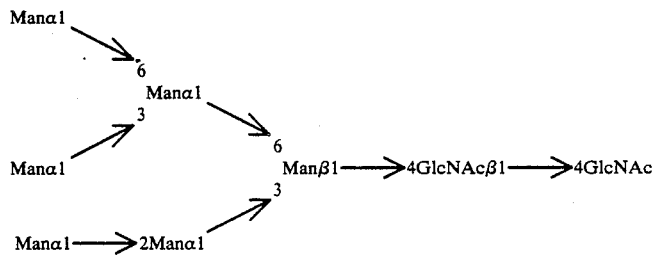

C-H

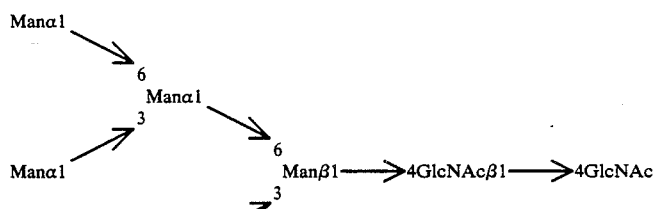

C-I

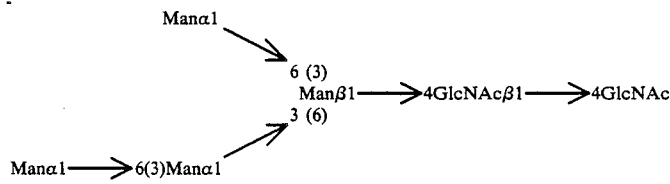

C-J

DETAILED DESCRIPTION OF THE INVENTION

Figure 1:
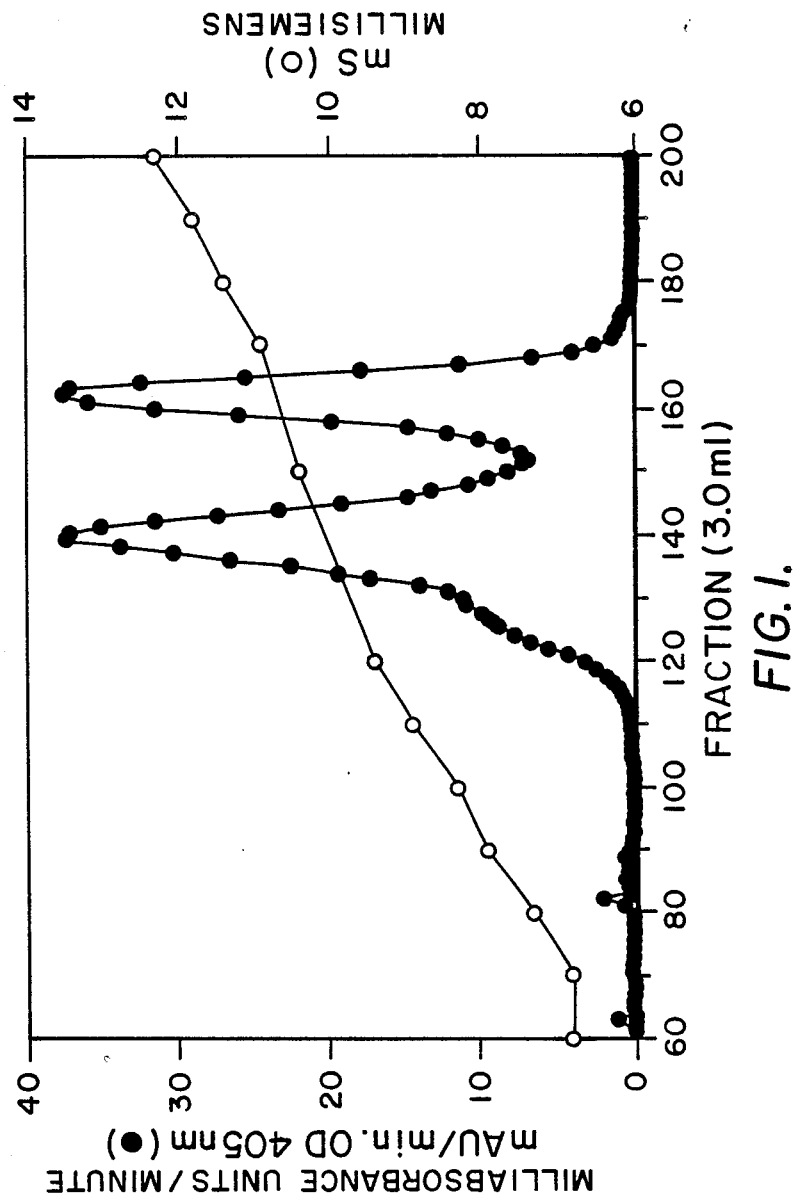

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which:

FIG. 1 is a graphical representation which shows the lysine-Sepharose column chromatography elution profile of the Type I and II t-PA glycoproteins derived from normal human colon fibroblast cells CCD-18Co in one embodiment of the invention. It can be seen that the two major peaks comprising the Type I and Type II fractions, respectively, do not represent the entire unfractionated t-PA.

Figure 2A:
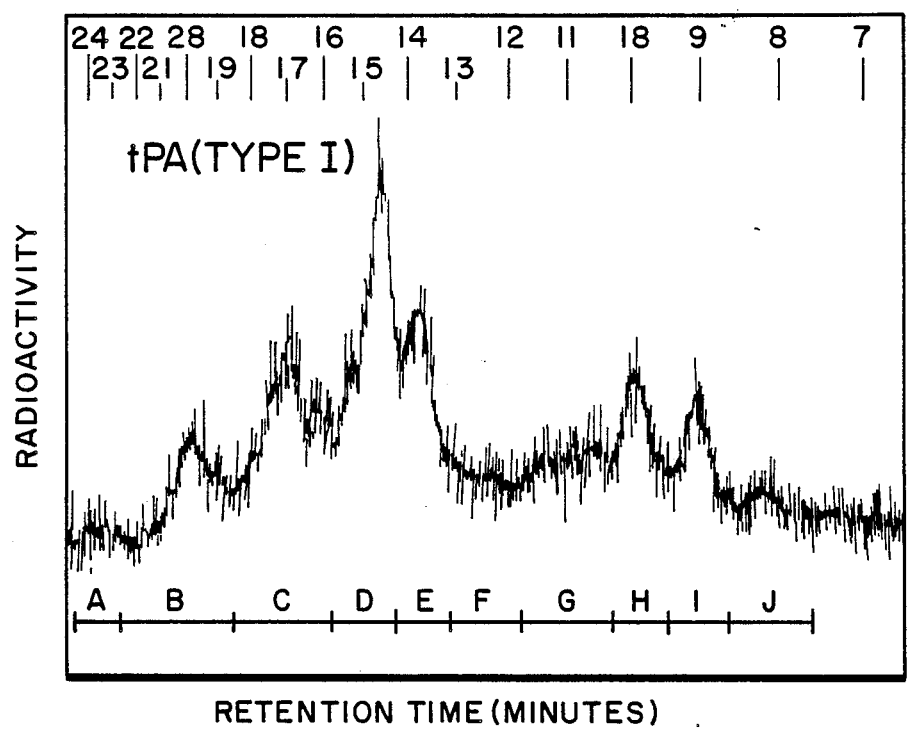
Figure 2B:
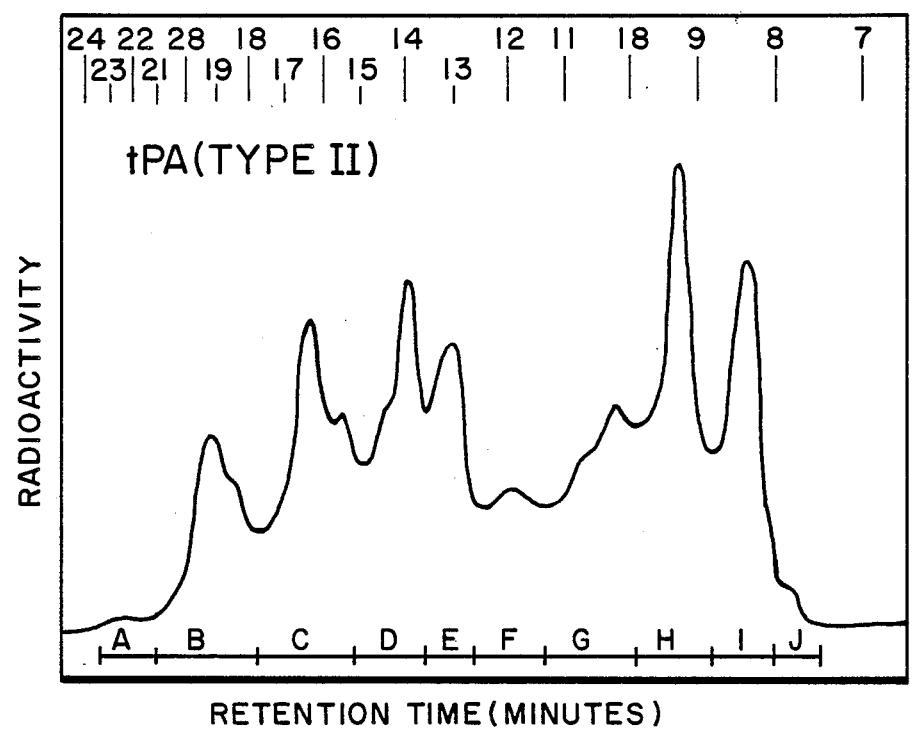
Figure 3A:
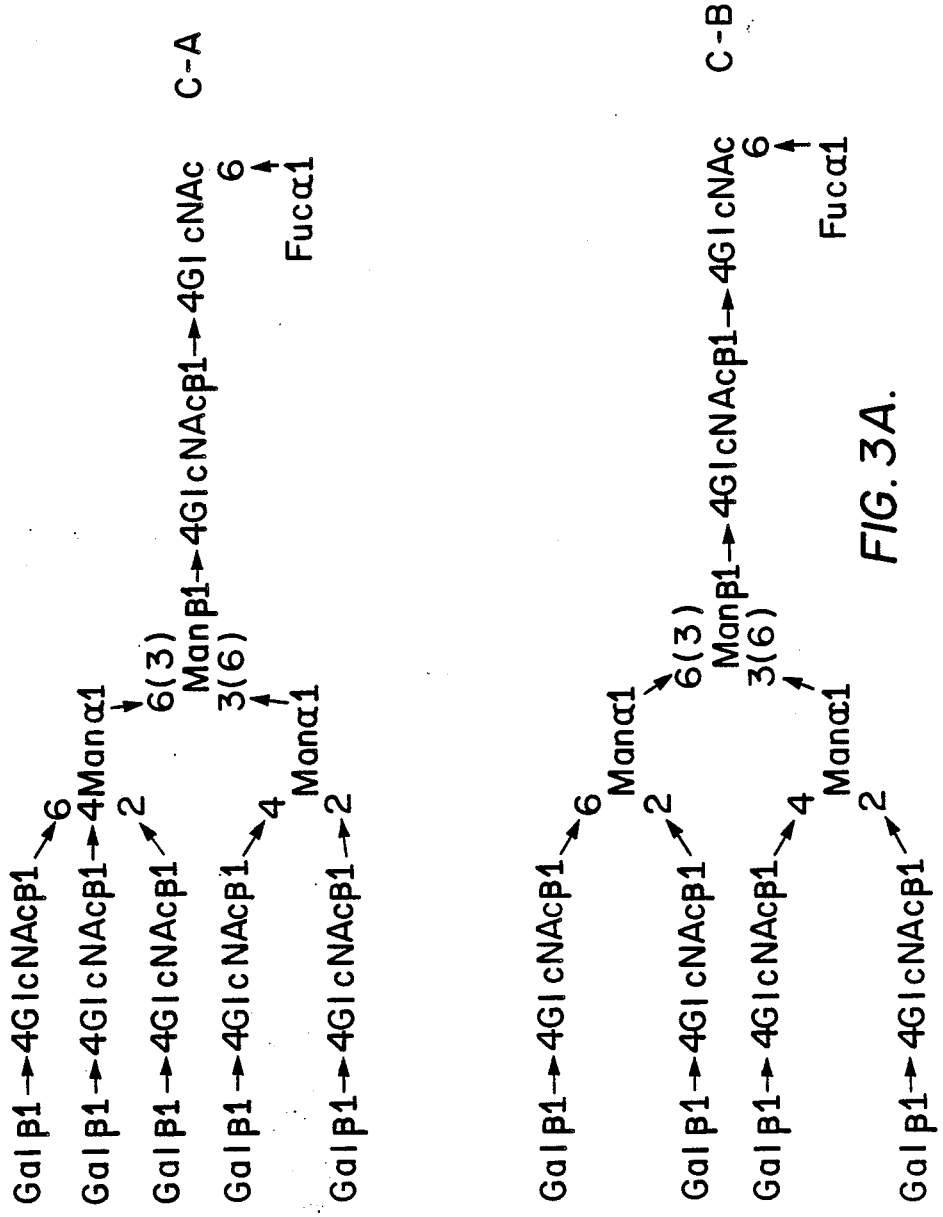
Figure 3B:
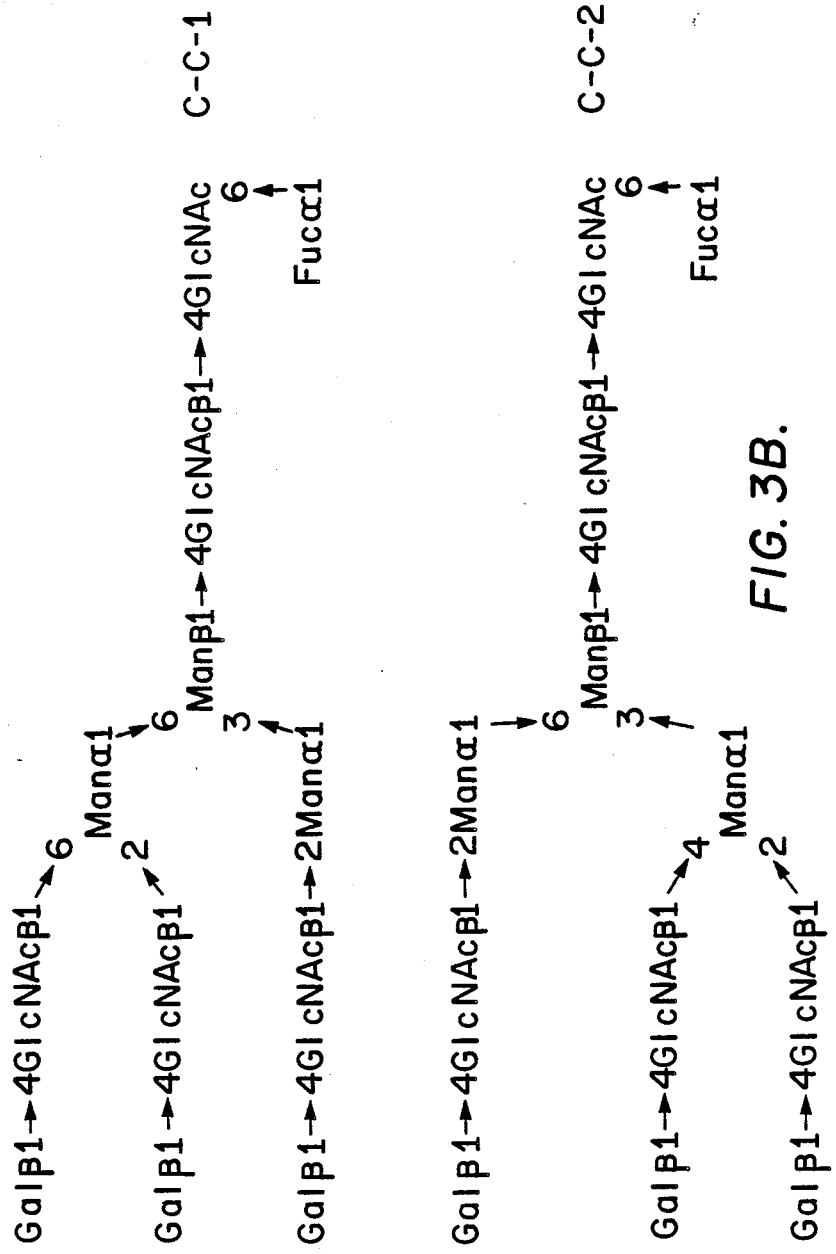
Figure 3C:
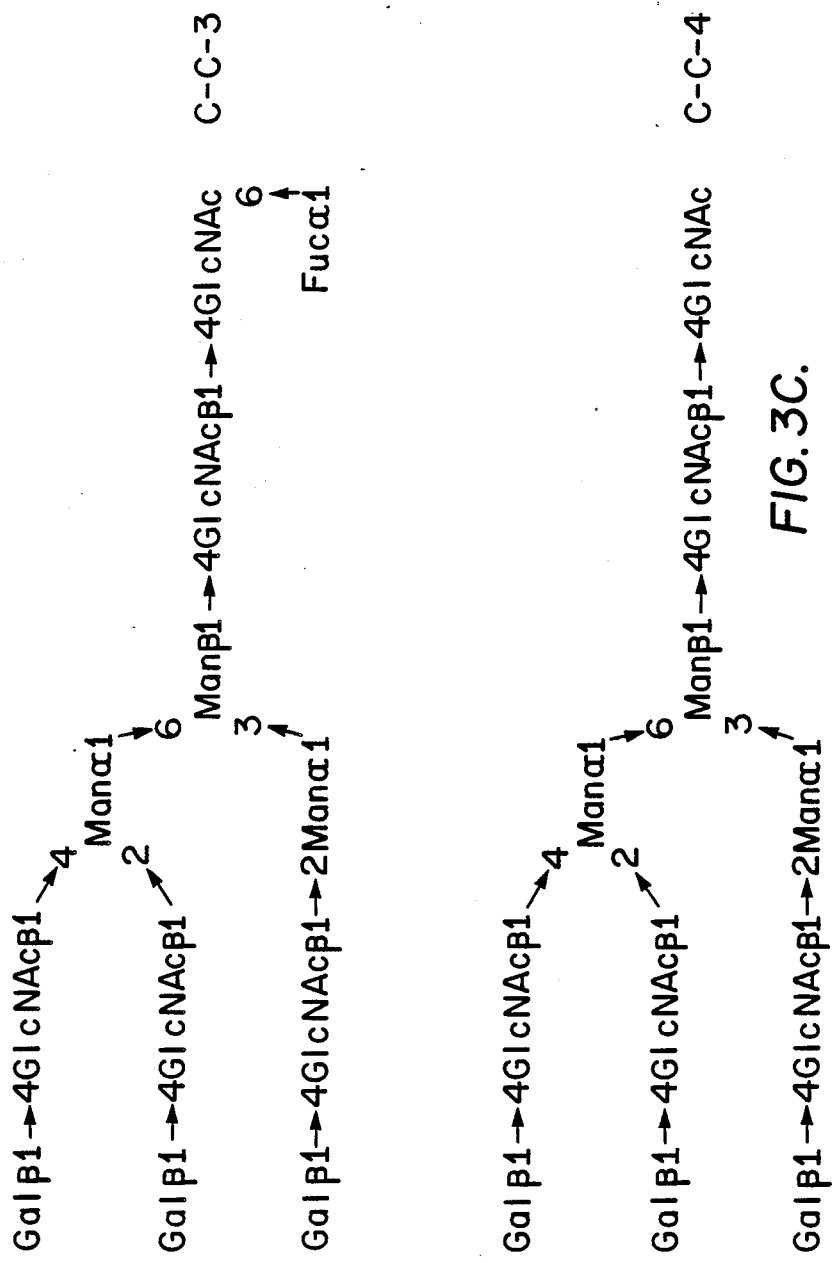
Figure 3D:
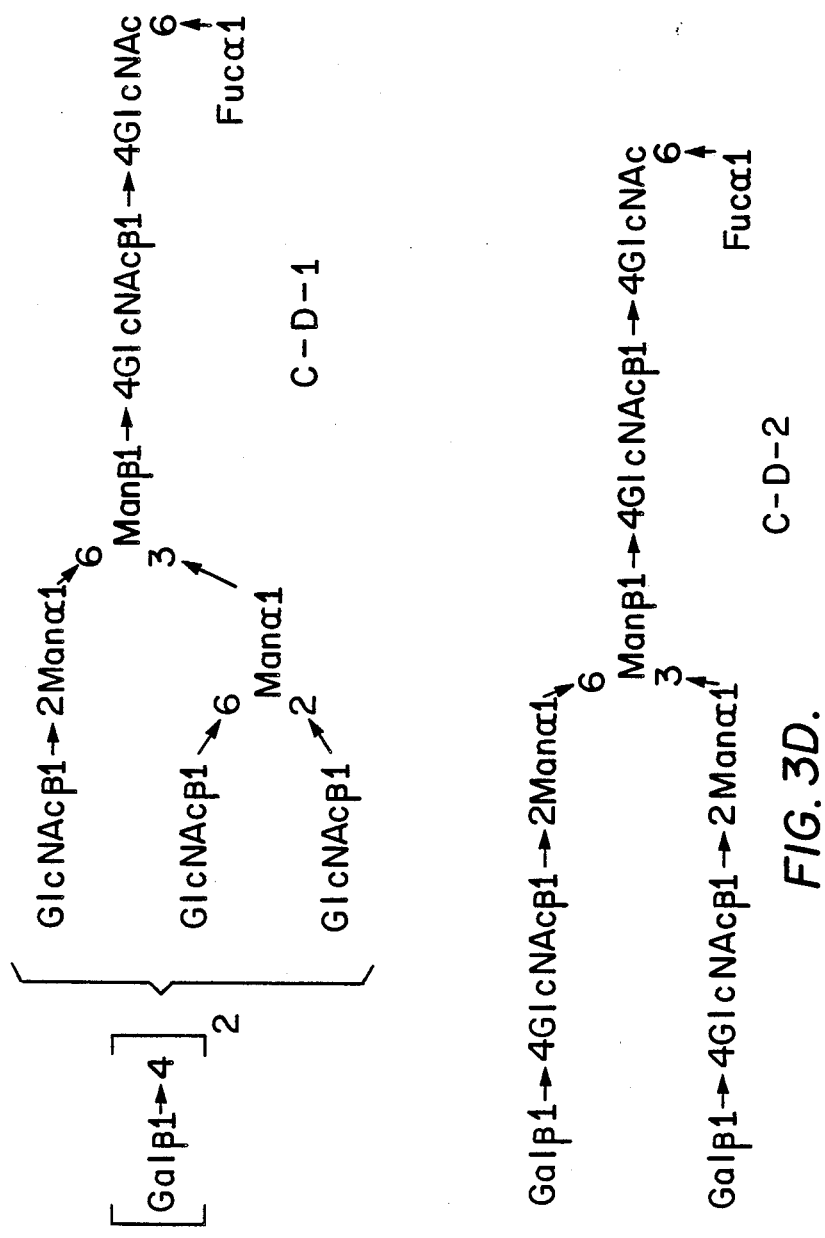
Figure 3E:
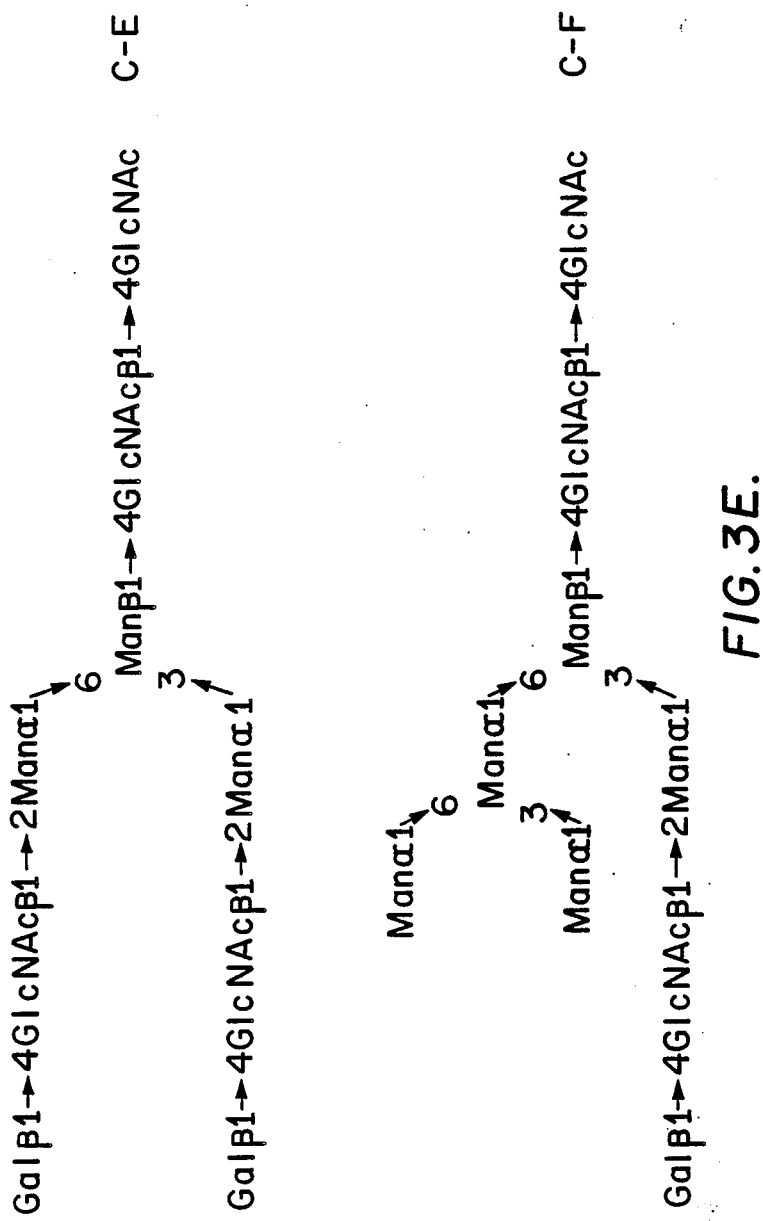
Figure 3H:
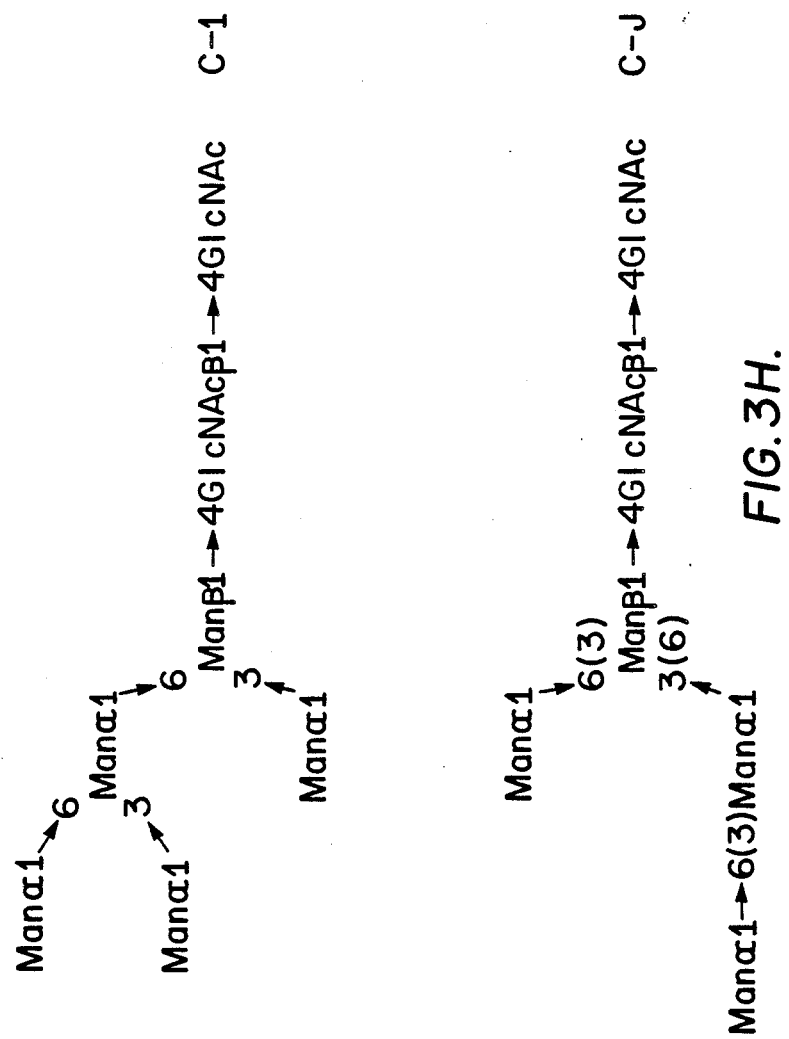
Figure 3F:
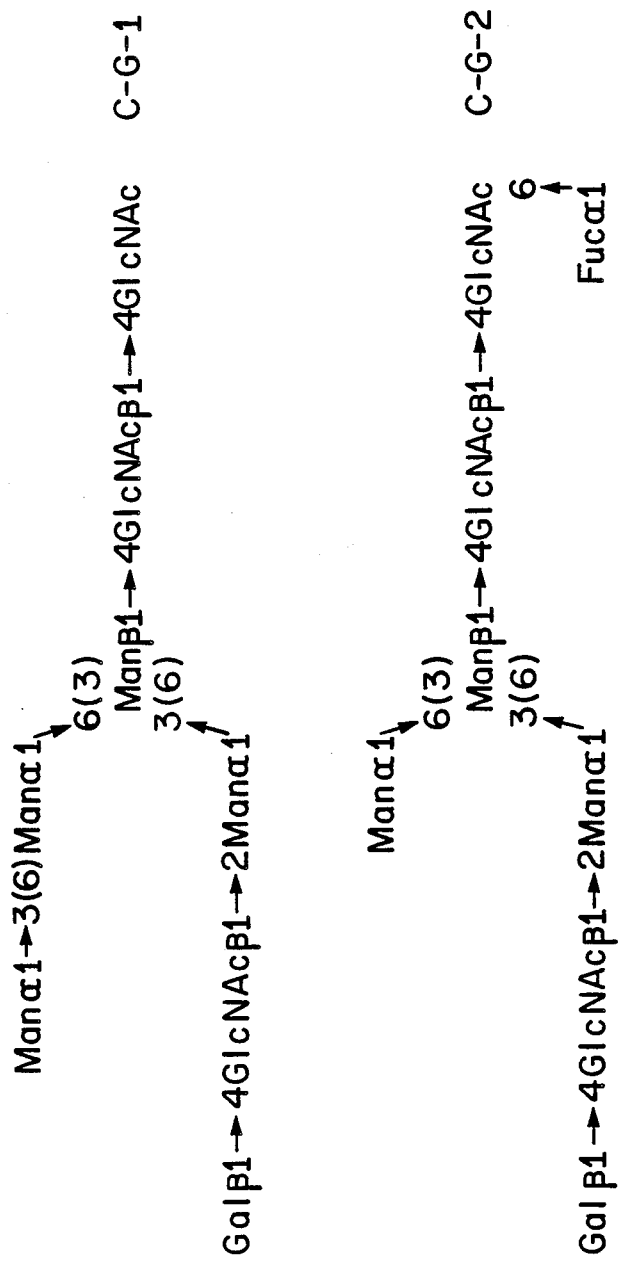
Figure 3G:
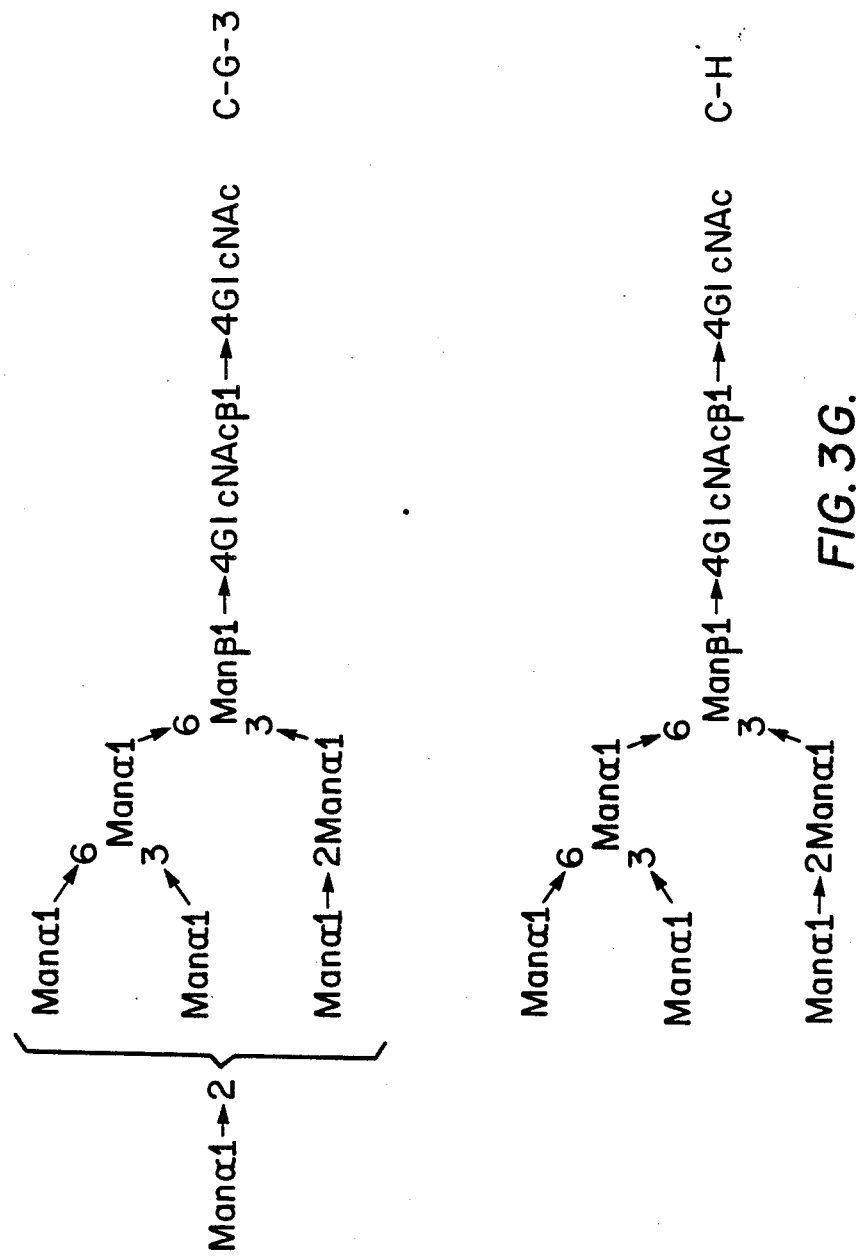

FIG. 2 is a graphical representation which shows the Bio-Gel P4 column chromatography elution profile of the oligosaccharides released from the Type I and Type II t-PA glycoproteins of FIG. 1 following neuraminidase digestion. Upper Panel A shows the Type I and lower Panel B the Type II elution profiles. The numbered arrows at the top indicate the elution positions of glucose oligomers in glucose units (g. u.); the letters at the bottom indicate the ten oligosaccharide fractions.

FIG. 3 shows the structures of the sixteen oligosaccharides liberated from the colon t-PA of FIG. 2. For convenience, the oligosaccharides are also designated by shorthand notation C-A to C-J shown to the right of each oligosaccharide, in the 3 sheets A, B and C of FIG. 3.

In these Figures and elsewhere herein, conventional carbohydrate abbreviations and nomenclature are used. Thus, the following symbols are used to indicate monosaccharide units and their residues in oligosaccharides:

| | |
|---|---|
| Glucose | Glc |
| Galactose | Gal |
| Mannose | Man |
| Fucose | Fuc |

Glyconic acids, glycuronic acids, 2-amino-2-deoxysaccharides, and their N-acetyl derivatives are designated by modified symbols. For example:

| | |
|---|---|
| N-Acetylglucosamine | GlcNAc |
| N-Acetylneuraminic acid | NeuNAc |

The position and nature of links between units are shown by numerals and the anomeric symbols $\alpha$ and $\beta$.

Arrows are used to indicate the direction of the glycoside link with the arrow pointing away from the hemiacetal carbon of the link. For example, a common branched core in oligosaccharides with N-glycosidic protein links can be represented as follows:

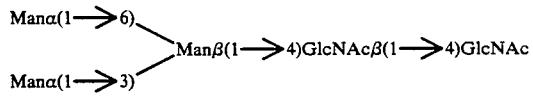

Determination of the structure of the oligosaccharides from the colon t-PA employs adaptation of the method used for Immunoglobulin G-derived asparagine-linked oligosaccharides as described by Rademacher and Dwek, *Prog. Immunol.* 5, 95–112 (1983); Parekh et al., *Nature* 316, 452–457 (1985); and U.S. Pat. No. 4,659,659. According to this method, the glycoprotein sample is subjected to controlled hydrazinolysis to release intact its associated oligosaccharide moieties as described by Takahasi et al., *Meth. Enzymol.* 83, 263–268 (1982). Reduction of the reducing terminal N-acetylglucosamine residues using $NaB^3H_4$ is then performed to label radioactively each carbohydrate chain. Each labeled oligosaccharide mixture is then subjected to exhaustive neuraminidase digestion in order to analyze the distribution of neutral structures. The resulting 'asialo' oligosaccharide mixtures are then fractionated by Bio-Gel ® P-4 (~400 mesh) gel filtration chromatography, which separates neutral oligosaccharides on the basis of the effective hydrodynamic volumes as described by Yamashita et al., *Meth. Enzymol.* 83, 105–126 (1982). Bio-Gel P-4 is a gel filtration material of choice for analysis of reduced oligosaccharides by high voltage gel permeation chromatography due to the polyacrylamide structure. Bio-Gel P is prepared by copolymerization of acrylamide with N,N'-methylene bis-acrylamide. P-4 has an exclusion limit and fractionation range of about 800–4000 daltons. This well-known gel filtration material is commercially available from Bio-Rad Laboratories Richmond, Calif.

The oligosaccharides also can be initially isolated from the t-PA glycoprotein by the preparative scale methods described in U.S. Pat. No. 4,719,294 and in application Ser. No. 929,962, filed Nov. 12, 1986. Said methods employ hydrazinolysis of the glycoprotein under reaction conditions to cause cleavage at the N-linked sites, producing a mixture having as a major component a de-N-acetylated hydrazone derivative of the oligosaccharides, followed by N-acylation of the hydrazone derivative, acid-catalysis of the hydrazone derivative, preferably followed by treatment with a stoichiometric amount of Cu(II) ions, to produce unreduced oligosaccharides, and subjecting the resulting unreduced oligosaccharides to cellulose column chromatography to remove contaminants and to recover the unreduced oligosaccharides. The latter materials, being essentially pure, can be used for attachment to various peptide or protein chains for further study.

Oligosaccharides can be determined by the use of enzymes which are specific for their hydrolysis coupled with or followed by enzymic reactions which allow measurement of a product of hydrolysis. Thus, two useful enzymes for exoglycosidase digestion are Jack bean $\beta$-N-acetylhexosaminidase and Jack bean $\alpha$-mannosidase which are commercially available from the Sigma Chemical Company (Poole, England) and can be further purified by adaptation of the method of Li and Li, *Meth. Enzym.* 28, 706 (1972). Jack bean $\beta$-N-acetylhexosaminidase cleaves all non-reducing terminal $\beta$-linked GlcNAc residues. Jack bean $\alpha$-mannosidase will liberate one mannose from R-Man$\alpha$-1→6(Man$\alpha$1→3)R' but none from R-Man$\alpha$1→3(Man$\alpha$1→6)R' [R≠H] as described by Yamashita et al., *J. Biol. Chem.* 255, 5635 (1980). Another useful enzyme is Jack bean $\beta$-galactosidase which can be purified from Jack bean meal and cleaves all non-reducing terminal galactose residues linked via a $\beta$1→4 glycosidic bond. Still another enzyme for the exoglycosidase digestion is the $\beta$-N-acetylhexosaminidase from *Streptococcus pneumonia* which can be purified by adaptation of the procedure of Glasgow et al, *J. Biol. Chem.* 252, 8615 (1977). This enzyme will cleave a non-reducing terminal GlcNAc residue if this is part of the structure.

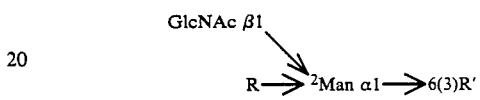

where R can be either H or GlcNAc$\beta$1→4 as described by Yamashita, *Biochem. Biophys. Res. Commun.* 100, 226 (1981). So also, the enzyme $\alpha$1→2 Mannosidase from *Aspergillus phoenicis* can be purified by adaptation of the procedure of Ichishima et al, *Biochem. Biophys. Acta* 658, 45 (1981). This enzyme will release non-reducing terminal mannose residues only if these are linked to the parent oligosaccharide via an $\alpha$1→2 glycosidic bond as described by Yamashita et al., *Biochem. Biophys. Res. Commun.* 96, 1335 (1980). The following other exoglycosidases also can be obtained from commercial sources in a form sufficiently pure for sequence analysis: $\alpha$-fucosidase from bovine epidydimis (Sigma Chemical Company, Poole, England), $\beta$-mannosidase fromm snail (Seikagaku Kogyo Company, Tokyo, Japan), and neuraminidase from *Arthrobacter ureafaciens* (Calbiochem).

Asparagine-linked oligosaccharides which are released by the hydrazinolysis method, purified, tritium-labeled, treated with neuraminidase, and the resulting asialo oligosaccharides fractionated by the gel-permeation chromatography can then be analyzed by a sequence of exoglycosidase digestions with the foregoing enzymes. By comparing the initial elution positions and the exoglycosidase reactivity of oligosaccharides of known sequence, the structure of the released oligosaccharides can be determined. See, for example, Kobata in "Biology of Carbohydrates," Ginsberg and Robbins, Eds., John Wiley and Sons, pp. 87–162, 1984; Snider, Ibid., pp. 163–193.

The following detailed examples will further illustrate the invention although it will be understood that the invention is not limited to these specific examples.

EXAMPLE 1

CCD-18Co cells sub-cultured from cells originally obtained from the American Type Culture Collection (ATCC CRL-1459) were grown at 37° C. in roller bottles using Dulbecco's MEM high glucose medium supplemented with 10% fetal bovine serum. The resulting cells were then cultured at 37° C. in the same medium in larger scale microcarrier suspension culture in 12 liter reactors using Corning Geli-Bead microcarriers.

After a suitable growth period, the pH of the conditioned media was adjusted to 5.6 and bulk purified by cation-exchange chromatography essentially by the method described by Kruithof et al., *Biochem. J.* 226, 631-636 (1985), except that the cation exchange resin used was S-Sepharose ®, Fast Flow, which is a strong cation exchanger commercially available from Pharmacia. The bulk purification was followed by immunoaffinity chromatography using t-PA monoclonal antibodies essentially by the method described by Einarsson et al., *Biochim. Biophys. Acta* 830, 1-10 (1985), and then HPLC gel filtration using a TSK 3000 SW column equilibrated with 1.6M KSCN, 20 mM sodium phosphate buffer and 0.01% Tween ® 80, pH 6.8. The purified t-PA material was then concentrated using an Amicon ® pressure concentration cell and a hydrophilic (YM-10) membrane and exchanged into 1M ammonium bicarbonate using a Sephadex ® G-25 gel filtration column prior to application to a 1.6 cm I.D.×96 cm lysine-Sepharose 4B column for separation into Type I and Type II glycoproteins.

The Lysine-Sepharose affinity chromatography was carried out as follows:

Sixty grams of Lysine-Sepharose 4B resin (Pharmacia, Piscataway, N.J.) was hydrated 48 hours at room temperature (rt) in equilibration buffer containing Sigma phosphate buffered saline (PBS) (120 mmol/L NaCl, 2.7 mmol/L KCl, 10 mmol/L phosphate), 0.01% Tween ® 20 (polysorbate 20) (Pierce, Rockford, IL), 0.01% sodium azide, and 0.2M KSCN, pH adjusted to 8.0 using saturated NaOH. The equilibration buffer conductivity was adjusted to 0.0066 prior to use.

Using a large filter funnel, the resin was washed with 5 mg bovine serum albumin (BSA) in 10 mls of equilibration buffer, 500 mls equilibration buffer, 500 mls elution buffer containing 0.6M Arginine-HCl in Sigma PBS with 0.01% Tween 20, 0.01% sodium azide, and 0.25M KSCN, pH 8.0, and an additional 1 L equilibration buffer, in that order.

The resin slurry was vacuum deaerated and the column was poured using a thick slurry and a single settling in order to minimize flow irregularities. The column was then moved from rt to a 4° C. chamber, at which temperature it was maintained. Both equilibration and elution buffers were prechilled before usage. However, conductivity was always measured after buffers or column fractions were equilibrated to room temperature since conductivity is a temperature dependent property. Five column volumes equilibration buffer were passed through the column prior to initial sample application.

Sample application: 3.8 mg t-PA was applied to the column in 1M ammonium bicarbonate. Elution characteristics were unchanged whether column was washed with 200 mls or 40 mls of the equilibration buffer before starting gradient elution. Therefore, after applying the sample, the column was washed with a minimum of 40 mls of equilibration buffer. A linear gradient was formed using 250 mls of equilibration buffer in the first chamber and 250 mls of elution buffer in the second chamber of a Pharmacia gradient mixer (GM-1 model). Fractions were collected in drop mode, 72 drops per fraction (3.0 ml) at a flow rate approximately 0.15 ml per minute or 9 ml per hour. Conductivity and amidolytic activity were routinely measured for fractions 61-200.

Amidolytic Activity: Synthetic chromogenic substrate 2322 (H-D-Val-Gly-Arg-paranitroanilide) (KabiVitrum, Stockholm, Sweden) was used for an amidolytic assay of enzymatic activity based on the method of Rijken and Collen, *J. Biol. Chem.*, 256(13), 7035-7045 (1981). Amidolytic activity was used as a rate assay in which absorbance was measured at a number of timepoints until an absorbance of 400 mAU was reached, and the slope (mAU/min) of the absorbance vs time plot was calculated.

FIG. 1 shows the Lysine-Sepharose elution profile in which fractions 131-145 comprise the Type I t-PA and fractions 156-170 comprise the Type II t-PA.

EXAMPLE 2

An analysis of the N-linked oligosaccharides of the Type I and Type II t-PA fractionated by lysine-Sepharose affinity chromatography in Example 1 was made by the method described hereinbefore and as described in Example 2 of copending application Ser. No. 929,950. According to this method, asparagine-linked oligosaccharides were released, purified, and tritium-labelled from each of Type I and Type II t-PA. The oligosaccharides so released were treated with neuraminidase, and the resulting asialo oligosaccharides fractionated by gel-permeation chromatography. As previously, all acidic oligosaccharides were rendered neutral by neuraminidase treatment.

The asialo oligosaccharide gel-permeation chromatograms generated from each of Type I and Type II t-PA are shown in FIG. 2. Individual oligosaccharide fractions were pooled as described previously. The nomenclature adopted previously for individual asialo oligosaccharide fractions and structures is used herein.

Oligosaccharide fractions C-C, C-D, and C-G contain several oligosaccharide structures, namely, C-C-1,2,3 and 4; C-D-1 and 2; and C-G-1,2 and 3; respectively. The relative incidence of C-C-1, C-C-2, C-C-3, C-C-4, C-D-1, C-D-2, C-G-1, C-G-2 and C-G-3, in each of Type I and Type II t-PA was determined by the sequence of exoglycosidase digestions as described previously. The relative molar ratios of individual asialo oligosaccharide structures released from each of type I and type II t-PA are given in Table II, together with the values for the unfractionated t-PA.

TABLE II

| Oligosaccharide fraction | Oligosaccharide | % type I | % type II | % unfractionated |
| --- | --- | --- | --- | --- |
| C-A | C-A | 2 | 2 | 1 |
| C-B | C-B | 9 | 10 | 7 |
| C-C | C-C-1 | 12 | 10 | 11 |
|  | C-C-2 | 3 | 3 | 3 |
|  | C-C-3 | 2 | 1 | 2 |
|  | C-C-4 | 2 | 1 | 1 |
| C-D | C-D-1 | 5 | 3 | 5 |
|  | C-D-2 | 17 | 9 | 15 |
| C-E | C-E | 13 | 9 | 12 |
| C-F | C-F | 6 | 5 | 6 |
| C-G | C-G-1 | 3 | 6 | 4 |
|  | C-G-2 | 3 | 3 | 2 |
|  | C-G-3 | 4 | 5 | 4 |
| C-H | C-H | 9 | 18 | 14 |
| C-I | C-I | 8 | 14 | 12 |
| C-J | C-J | 3 | 3 | 3 |

The percentages for each oligosaccharides in the foregoing Table I are estimated to be subject to variation of ± one unit of the values shown.

By current and well-established convention, oligosaccharides C-A, C-B, C-C-1, C-C-2, C-C-3, C-C-4, C-D-1, C-D-2, C-E, and C-G-2 are deemed to be of the complex class, while oligosaccharides C-F and C-G-1 are deemed to be of the hybrid class, and oligosaccharides C-G-3, C-H, C-I, and C-J are deemed to be of the oligomannose class. Using the information contained within Table II, the relative incidence of complex, hybrid, and oligomannose structures in each of Type I and Type II t-PA was calculated. The results are provided in Table III, together with the relevant values for the unfractionated t-PA.

TABLE III

|  | type I | type II | unfractionated |
|---|---|---|---|
| % Complex | 68 | 51 | 67 |
| % Hybrid | 9 | 10 | 6 |
| % Oligomannose | 23 | 39 | 28 |

The colon Type I and Type II t-PA of the invention can be used for the treatment of thrombolytic conditions by suitable administration to a patient in need of such treatment. The amount of the t-PA which would normally be administered is primarily dependent upon the physical characteristics of the recipient and the severity of the thrombolytic condition. The amount to be administered must be an effective amount, that is, an amount which is medically beneficial but does not present toxic effects which overweigh the advantages which accompany its use. The preferable route of administration is parenteral, especially intravenous. Intravenous administration of the t-PA in solution with normal physiologic saline is illustrative. Other suitable formulations of the active t-PA in pharmaceutically acceptable diluents or carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. Human color fibroblast tissue plasminogen activator glycoprotein in which the protein moiety is glycosylated with Type I or Type II glycoforms or mixtures thereof upon separation by affinity chromatography on lysine-Sepharose such that the percent molar ratio of the individual oligosaccharides is about as follows:

| Oligosaccharide | Percentage |
|---|---|
| C-A | 1–3 |
| C-B | 8–11 |
| C-C-1 | 9–13 |
| C-C-2 | 2–4 |
| C-C-3 | 0–3 |
| C-C-4 | 0–3 |
| C-D-1 | 2–6 |
| C-D-2 | 8–18 |
| C-E | 8–14 |
| C-F | 4–7 |
| C-G-1 | 2–7 |
| C-G-2 | 2–4 |
| C-G-3 | 3–6 |
| C-H | 8–19 |
| C-I | 7–15 |
| C-J | 2–4. |

2. A therapeutic composition for producing thrombolysis comprising a therapeutically effective amount of the tissue plasminogen activator of claim 1 and a pharmaceutically acceptable carrier or diluent.

3. A method for producing thrombolysis in a patient requiring thrombolytic activity comprising administering to said patient a therapeutically effective amount of the tissue plasminogen activator of claim 1.

* * * * *